United States Patent [19]

Gullo et al.

[11] 4,157,392

[45] Jun. 5, 1979

[54] PHARMACOLOGICALLY ACTIVE SUBSTITUTED 1,2,4-TRIAZINES

[75] Inventors: James M. Gullo, Perry; William P. Heilman, Chagrin Falls; Robert J. Wayner, Fairport Harbor; Robert E. Moser, Mentor, all of Ohio

[73] Assignee: Diamond Shamrock Corporation, Cleveland, Ohio

[21] Appl. No.: 897,803

[22] Filed: Apr. 19, 1978

Related U.S. Application Data

[63] Continuation-in-part of Ser. No. 797,676, May 17, 1977, abandoned.

[51] Int. Cl.² .................. C07D 253/06; A61K 31/53
[52] U.S. Cl. .................................. 424/249; 544/182; 544/112
[58] Field of Search ................ 544/182, 112; 424/249

[56] References Cited

U.S. PATENT DOCUMENTS

| | | | |
|---|---|---|---|
| 3,007,927 | 11/1961 | Liberman | 544/182 |
| 3,077,473 | 2/1963 | Liberman | 544/182 |
| 3,948,894 | 4/1976 | Lacefield | 544/182 |
| 4,013,654 | 3/1977 | Lacefield | 544/182 |

FOREIGN PATENT DOCUMENTS

| | | | |
|---|---|---|---|
| 554014 | 3/1958 | Canada | 544/182 |
| 1099846 | 2/1961 | Fed. Rep. of Germany | 544/182 |
| 881340 | 11/1961 | United Kingdom | 544/182 |

OTHER PUBLICATIONS

Grundmann et al., *Journal of Organic Chemistry*, vol. 23, pp. 1522-1524, (1958).

*Primary Examiner*—John M. Ford
*Attorney, Agent, or Firm*—Stuart L. Melton

[57] ABSTRACT

Substituted 1,2,4-triazines, compositions thereof and methods of using same are described. The compounds of the invention exhibit a wide range of pharmacological activity including anti-inflammatory, analgesic, antipyretic, hypotensive and central nervous system effects.

13 Claims, No Drawings

PHARMACOLOGICALLY ACTIVE SUBSTITUTED 1,2,4-TRIAZINES

CROSS-REFERENCE TO RELATED APPLICATION

This application is a continuation-in-part of copending application Ser. No. 797,676, filed May 17, 1977, now abandoned.

BACKGROUND OF THE INVENTION

The present invention relates generally to 1,2,4-triazine compounds and, more particularly, to certain substituted triazines evidencing anti-inflammatory, analgesic, anti-pyretic, hypotensive and central nervous system activity in warm-blooded animals.

Substituted 1,2,4-triazine compounds having various substituents thereon have heretofore been prepared and suggested for use in different ultimate applications. For example, Buu-hoi et al found that 3-mercapto-5,6-dimethyl-1,2,4-triazine is tuberculostatic in vitro (J. Chem. Soc., 1956, 713–16). Likewise, 3-amino-6-alkyl(or 5-nitrofurylethenyl)-1,2,4-triazines have been suggested as having antibacterial and antiviral activity (Cf. Chemical Abstracts, Vol. 60, 9278 g and Vol. 62, 9155d). Japanese Pat. No. 69-08866 (Apr. 24, 1969) also describes the bactericidal activity of 3-amino-5-alkoxy-6-methyl-1,2,4-triazines.

With respect to the anti-inflammatory activity of as-triazine compounds, U.S. Pat. No. 3,948,894 discloses 3-amino-5,6-diaryl-1,2,4-triazine compounds and more specifically, 3-alkylamino, hydroxy-alkylamino, piperazino, piperidino, morpholino or pyrrolidino-5,6disubstituted phenyl, i.e., alkoxy, fluoro, dimethylamino or methylsulfinylphenyl triazine compounds and the treatment of inflammation, swelling, fever and ossification in warm-blooded animals therewith. The foregoing compounds are indicated to be active upon oral or parenteral administration, whereas Belgian Pat. No. 839,469 discloses 3-unsubstituted and 3-$C_1$-$C_8$ alkyl, $C_7$-$C_8$ aralkyl, $C_3$-$C_8$ cycloalkyl, $C_4$-$C_8$ (cycloalkyl)-alkyl or the corresponding oxygen or thioethers, and halo-, $C_1$-$C_3$ alkyl-, $C_1$-$C_3$ alkoxy- or di($C_1$-$C_3$ alkyl) amine-5,6-substituted phenyl-1,2,4-triazines as anti-inflammatory agents which are topically active. U.S. Pat. No. 3,989,831 also discloses 3-chloro-5,6-diaryl-1,2,4-triazines as topically active anti-inflammatory compounds. U.S. Pat. No. 3,644,358 describes a series of 3-and 6-alkoxycarbonyl or carboxamido substituted 1,2,4-triazines having anti-inflammatory activity.

In Japanese Pat. No. 74-27874 (July, 1974), the patentees describe 3-amino, methylamino or 4-methyl-1-piperazinyl-5-(4'-pyridyl)-1,2,4-triazines as having anti-inflammatory activity.

Other asymmetrical triazines have been suggested as having antihypertensive activity. For example, U.S. Pat. No. 3,007,927 discloses 3,5-dihydrazino or 3,5-dihydrazino-6-lower alkyl-1,2,4-triazines as exhibiting a strong vasodilatory effect. Similarly, 3-hydrazino-5-phenyl-1,2,4-triazine is indicated to be a moderately active antihypertensive agent. See Burger, Medicinal Chemistry, 3rd Ed., 1027, (Wiley Interscience, 1970).

With respect to central nervous system activity, Trepanier et al, J. Med. Chem. 9, 881–885 (1966) disclose certain substituted 1,4,5,6-tetrahydro-1,2,4,-triazine as having anticonvulsant activity.

In addition to the foregoing, it is noted that 3-methylthio-5-phenyl-, 3-methylthio-5,6-dimethyl-, 3-methoxy-5,6-dimethyl-, 3-hydrazino-5,6-dimethyl-, and 3-methoxy-5-phenyl-1,2,4,-triazines are described in Paudler and Chen, J. Hetero. Chem. 7, 767–771 (1970). Laakso describes the 3-ethoxy-5-phenyl-1,2,4-triazine (Tetrahedron, 1, 103 (1957)). 3-Hydroxy-5,6-diphenyl-1,2,4-triazine is described in Thiele, Ann. Chem., 302, 299, 1890. No biological or other utility for these compounds is mentioned in the foregoing literature publications.

SUMMARY OF THE INVENTION

It is, therefore, a primary object of the present invention to afford novel substituted 1,2,4,-triazine compounds which evidence unexpectedly superior pharmacological activity or different properties compared to previously proposed triazine compounds in warm-blooded animals.

A further object of the present invention is to provide method for inducing or obtaining antiphlogistic, analgesic, hypotensive and psychotropic effects in mammals by the administration of preselected dosages of active substituted 1,2,4-triazine compounds or pharmaceutically acceptable salts thereof in suitable non-toxic pharmaceutical dosage unit forms or compositions.

A still further object of the present invention is to provide stable, non-toxic dosage unit forms adapted for, e.g., oral, rectal, parenteral, etc. administration useful in the promotion of analgesia or central nervous system effects and the treatment, management or mitigation of fever, inflammatory or hypertensive conditions or disorders.

These and other similar objects, advantages and features are accomplished according to the methods, products and compositions of the invention comprised of substituted-1,2,4-triazines, compositions derived therefrom and methods employing same.

DESCRIPTION OF THE PREFERRED EMBODIMENTS

It has now been found, in accordance with the present invention, that substituted 1,2,4-triazines of the general formula I

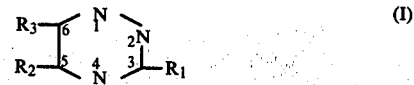

wherein
$R_1$ represents hydrazino, $C_1$-$C_4$ alkylhydrazino,

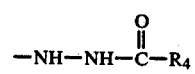

where $R_4$ is $C_1$-$C_8$ alkyl, $C_1$-$C_8$ alkenyl, halo ($C_1$-$C_8$) alkyl, halo ($C_1$-$C_8$) alkenyl, $C_6$-$C_{10}$ cycloalkyl or a group of the formula

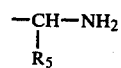

where $R_5$ is H, $C_1$-$C_4$ alkyl or benzyl and the corresponding N-amino carbobenzyloxy derivatives thereof (i.e.,

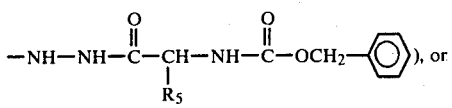

hydroxy $C_1$-$C_4$ alkylamino, N-($C_1$-$C_2$ alkyl)-N-(hydroxy $C_1$-$C_4$ alkyl) amino, $C_1$-$C_{10}$ alkoxy, $C_6$-$C_{10}$ aryloxy, $C_3$-$C_6$ cycloalkoxy, phenylalkoxy, alkyl ($C_1$-$C_4$) aryloxy (aryl as before), allyloxy, helophenoxy, $C_1$-$C_4$ alkylphenoxy, $C_1$-$C_4$ alkoxyphenoxy, $C_3$-$C_6$ cycloalkylthio $C_1$-$C_4$ alkylsulfinyl, $C_1$-$C_4$ alkylsulfonyl, phenylalkyl (e.g., $C_1$-$C_4$ alkyl) thio, cis-dimethylpyrrolidyl or pyridyl;

- $R_2$ represents hydrogen, $C_1$-$C_4$ alkyl, aryl (e.g., phenyl, naphthyl, anthracenyl), $C_3$-$C_6$ cycloalkyl, adamantyl, furyl, thienyl, benzofuryl, indolyl, pyridyl, halothienyl, phenyl or phenyl substituted with at least one substituent selected from halo, $C_1$-$C_6$ alkyl, halo ($C_1$-$C_6$) alkyl, $C_1$-$C_6$ alkoxy, acetamido, benzyloxy diphenylmethyl, morpholino, methylenedioxy and nitro;
- $R_3$ represents hydrogen, $C_1$-$C_6$ alkyl, aryl, pyridyl, furyl or phenyl substituted with at least one substituent selected from halo, $C_1$-$C_6$ alkyl, $C_1$-$C_6$ alkoxy, methylenedioxy and acetamido,
- with the proviso that when $R_2$ is hydrogen $R_3$ is also hydrogen; and the pharmaceutically acceptable acid addition salts thereof are useful anti-inflammatory, analgesic, anti-pyretic, hypotensive and psychotropic agents.

The substituted asymmetric triazine compounds of the present invention may be prepared by several alternative methods previously employed in the synthesis of 1,2,4-triazines or modifications thereof to obtain the $R_1$, $R_2$ or $R_3$ substituents thereon as defined above. For example, 3-alkylthio, hydrazino or alkoxy-5-aryl-1,2,4,-triazines can be readily prepared according to the procedures set forth in W. W. Paudler and T. K. Chen, J. Hetero. Chem. 7, 767 (1970), wherein an appropriately substituted acetophenone is oxidized to the corresponding arylglyoxal by treatment with selenium dioxide. Condensation of S-methylthiosemicarbazide hydrogen iodide, obtained by the reation of thiosemicarbazide and methyl iodide, with an arylglyoxal affords the 3-methylthio-5-aryl-1,2,4,-triazine. The 3-methylthio-5-aryl substituted triazine may then be used as an intermediate for the preparation of the 3-hydrazino derivative by treatment with hydrazine hydrate or the 3-methoxy derivative by reaction with sodium methoxide. The foregoing general reaction scheme may be depicted as follows:

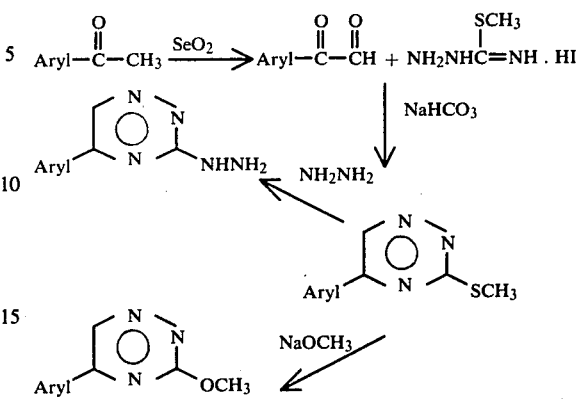

Compounds wherein $R_2$ and $R_3$ are as defined above may be synthesized according to the methods described by Polonovski et al, Compt. Rend., 238, 695 (1954). An appropriately substituted alpha-diketone is condensed with semicarbazide, followed by cyclization under basic conditions to form the 3-hydroxy-5,6-disubstituted-1,2,4-triazine. The last mentioned 3-hydroxy derivative is then chlorinated with phosphorus oxychloride to yield the 3-chloro-1,2,4-triazine which readily undergoes displacement by hydrazine or sodium methoxide to afford the 3-hydrazino-or 3-methoxy-5,6-disubstituted-1,2,4-triazine compounds, as shown in the following reaction scheme.

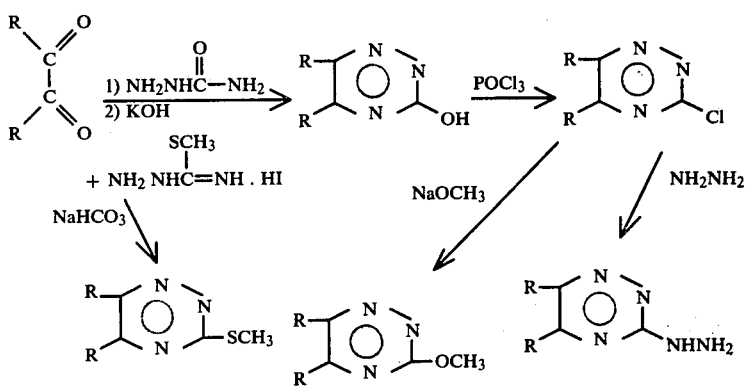

It is noted that the alpha-diketone starting material may be directly converted to the 3-methylthio-5,6-disubstituted-1,2,4-triazine by cyclization with S-methylthiosemicarbazide hydrogen iodide.

Reaction of the appropriate hydrazino triazine with the appropriate anhydride, acyl chloride or carbobenzyloxy (CBZ) amino acid affords the corresponding acyl hydrazine triazines or α-CBZ-amino acyl hydrazino triazines. Treatment of the CBZ amino acyl hydrazino triazines with concentrated HBr/acetic acid affords the free amino acid HBr salt.

Other substituents at the 3- position corresponding to $R_1$ as set forth hereinabove are readily obtained by formation of the corresponding 3-chloro-5,6-disubstituted-1,2,4-triazine. Facile substitution of the 3-chloro starting material is carried out with a variety of amines, alcohols, phenols, thiols, and the like to yield the corresponding 3-amino, alkoxy, phenoxy, alkylthio, etc. derivatives. Of course, similar substitution or displacement reactions may be carried out using the 3-methylthio reactant or intermediate.

Where necessary or desirable, the pharmaceutically or physiologically acceptable inorganic and organic acid addition salts of certain of the compounds of the present invention may be employed to, for instance, alter solubility properties or augment bioavailability. The criteria for selecting and methods for preparing salts suitable for administration are well known to those skilled in the art. Representative of acids for reaction with the sufficiently basic triazine compounds of the invention to form acceptable acid addition salts include hydrochloric, hydrobromic, hydroiodic, nitric, phosphoric, sulfuric, tartaric, citric, and the like. The expression "pharmaceutically acceptable" as used herein is intended to include those salts capable of being formed with the basic triazine compounds of the invention without materially altering the chemical structure or pharmacological properties of the parent triazine compounds. Additionally, compounds of the invention containing amino acid residues, i.e., an $\alpha$-amino acyl group, may be obtained as their hydrate salt form, such as mono- or di- hydrobromide, hydrochloride, etc. hydrate and such compounds constitute particularly advantageous water-soluble derivatives of the invention.

The synthesis methods described herein, in certain instances, result in the preparation of mixtures of triazine isomers, e.g., 5,6-position isomers which can be separated employing conventional crystallization or chromatographic techniques.

As previously indicated, the compounds of the present invention possess anti-inflammatory, anti-pyretic, analgesic, antihypertensive and central nervous system (e.g., hypnotic, sedative, antidepressant, muscle relaxant, spasmolytic, tranquilizing, etc.) effects. Of course, it will be appreciated that the specific response elicited upon administration of the compounds of the present invention to an animal species will vary depending upon the specific structure of the administered compound, the unit dose, dosage regimen and mode of administration, as well as the mammalian species involved. Accordingly, as detailed hereinbelow, certain of the compounds of the invention are preferred over others relative to a predetermined pharmacological activity.

Thus, as preferred compounds for use in the anti-inflammatory compositions and methods of the present invention, are those of Formula I wherein $R_1$ represents hydrazino, $C_1$-$C_4$ alkyl hydrazino,

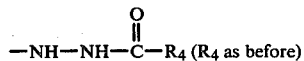

—NH—NH—C—R$_4$ (R$_4$ as before)

hydroxy $C_1$-$C_4$ alkyl amino, N-($C_1$-$C_2$ alkyl)-N-(hydroxy $C_1$-$C_4$ alkyl)amino, $C_1$-$C_{10}$ alkoxy, phenoxy, $C_1$-$C_4$ alkylphenoxy, $C_1$-$C_4$ alkoxyphenoxy, $C_1$-$C_{10}$ alkylthio (preferably, $C_1$-$C_4$ alkyl), or phenylalkyl (preferably, $C_1$-$C_4$ alkyl) thio; $R_2$ represents hydrogen, $C_1$-$C_4$ alkyl, $C_3$-$C_6$ cycloalkyl, phenyl, naphthyl, adamantyl, furyl, thienyl, benzofuryl, indolyl, pyridyl or phenyl substituted with at least one substituent selected from halo, $C_1$-$C_4$ alkyl, halo or perhalo ($C_1$-$C_6$) alkyl (e.g., trifluoromethyl, trifluoroethyl, etc.), $C_1$-$C_6$ alkoxy (including, e.g., 3',4'-dialkoxy), acetamido, morpholino or nitro; $R_3$ represents hydrogen, $C_1$-$C_6$ alkyl, phenyl, pyridyl or phenyl substituted with at least one substituent selected from $C_1$-$C_4$ alkyl, $C_1$-$C_6$ alkoxy, halo or acetamido; provided that when $R_2$ is hydrogen then $R_3$ is also hydrogen or when $R_1$ is hydroxyalkylamino or the group X—$R_6$ wherein X=O, or S, and $R_6$ is $C_1$-$C_8$ alkyl, $C_7$-$C_8$ aralkyl, $C_3$-$C_8$ cycloalkyl, $C_4$-$C_8$ cycloalkyl alkyl, $R_2$ and $R_3$ cannot simultaneously be halo-, alkyl-, or alkoxy-substituted phenyl; and the pharmaceutically acceptable acid addition salts thereof. Particularly preferred compounds of Formula I are those wherein $R_1$ is hydrazino, methylhydrazino, propionyl hydrazino, $\alpha$-aminoacetyl hydrazino, trifluoroacetyl hydrazino, hydroxy ($C_2$-$C_4$) alkylamino, $C_1$-$C_4$ alkoxy, allyloxy, $C_1$-$C_4$ alkylthio or benzylthio; $R_2$ is $C_1$-$C_4$ alkyl, phenyl, furyl, thienyl, pyridyl, indolyl, adamantyl, $C_3$-$C_6$ cycloalkyl or phenyl substituted with at least one substituent selected from halo (preferably, para-chloro, bromo or fluoro), halo $C_1$-$C_2$ alkyl (preferably, metal-trifluoromethyl), $C_1$-$C_4$ alkyl, $C_1$-$C_4$ alkoxy (preferably 3',4'-dimethoxy) and $R_3$ is hydrogen; or wherein $R_2$ and $R_3$ are the same and represent $C_1$-$C_4$ alkyl (preferably, methyl or ethyl), phenyl or pyridyl provided $R_1$ is selected from hydrazino, $C_1$-$C_4$ alkoxy (preferably, methoxy), allyloxy, $C_1$-$C_4$ alkylthio or benzylthio. As specifically preferred compounds of Formula I, there may be mentioned 3-methylthio-5-phenyl-1,2,4-triazine, 3-hydrazino-5-phenyl (or t-butyl)-1,2,4-triazine, 3-methylhydrazino-5-phenyl-1,2,4-triazine, 3-methoxy (or methylthio)-t-butyl-1,2,4-triazine, 3-methylthio-5-(2'-furyl or 2'-thienyl)-1,2,4-triazine, 3-trifluoroacetyl hydrazino-5-phenyl-1,2,4-triazine, 3-methoxy-5-(3'-trifluoromethyl phenyl)-1,2,4-triazine, 3-methylthio-5-(3'-trifluoromethyl phenyl)-1,2,4-triazine, 3-methoxy-5-(2'-furyl)-1,2,4-triazine, 3-ethoxy-5-phenyl-1,2,4-triazine, 3-propoxy-5-phenyl-1,2,4-triazine, 3-methylthio-5-cyclopropyl-1,2,4-triazine, 3-methoxy-5-cyclopropyl-1,2,4-triazine, 3-allyloxy-5-phenyl-1,2,4-triazine, 3-methylthio-5,6-dimethyl-1,2,4-triazine, 3-hydrazino-5,6-dimethyl-1,2,4-triazine, 3-methoxy-5,6-dipyridyl-1,2,4-triazine, 3-benzylthio-5,6-dimethyl-1,2,4-triazine and 3-methylthio-5-(3'-indolyl)-1,2,4-triazine.

Representative of preferred compounds of Formula I for use in the analgesic compositions and methods of the present invention are those wherein $R_1$ represents hydrazino, $C_1$-$C_4$ alkyl hydrazino, propionyl hydrazino, $\alpha$-amino propionylhydrazino, $\alpha$-amino-phenylpropionyl (phenylalanine) hydrazino, haloacyl hydrazino (preferably, trifluoroacetyl hydrazino), $C_1$-$C_4$ alkoxy or $C_1$-$C_4$ alkylthio, and $R_2$ represents $C_1$-$C_4$ alkyl (preferably, ethyl, t-butyl), thienyl, phenyl or phenyl substituted with at least one substituent selected from halo (preferably, meta-chloro), halo or perhalo ($C_1$-$C_4$) alkyl (preferably, meta-halomethyl), or $C_1$-$C_4$ alkoxy (preferably, para-methoxy) when $R_3$ is hydrogen; or compounds wherein $R_1$ is as defined before and $R_2$ and $R_3$ are the same and represent $C_1$-$C_4$ alkyl or $C_1$-$C_4$ alkoxyphenyl (preferably, para-methoxyphenyl). Based upon presently definable doseresponse relationships, especially preferred compounds falling within the aforesaid general Formula I are 3-hydrazino-5-phenyl (or meta-trifluoromethyl phenyl)-1,2,4-triazine, 3-methoxy-5-phenyl-1,2,4-triazine, 3-methoxy-5-t-butyl-1,2,4-triazine, 3-methylthio-5-(2'-thienyl)-1,2,4-triazine, 3-methylhydrazino-5-phenyl-1,2,4-triazine, 3-trifluoroacetyl hydrazino-5-phenyl-1,2,4-triazine, 3-methoxy (or methylthio)-5-(3'-trifluoromethyl phenyl)-1,2,4-triazine, 3-methoxy-5-(3'-chlorophenyl-1,2,4-triazine, 3-methylthio-5,6-dimethyl-1,2,4-triazine, 3-hydrazino-5,6-dimethyl-1,2,4-triazine and 3-methoxy (or methylthio)-5,6-(4'-methoxyphenyl)-1,2,4-triazine.

Inclusive of preferred compounds for use in the hypotensive compositions and methods of the present invention are compounds of Formula I, wherein $R_1$ represents hydrazino, $C_1$-$C_4$ alkyl hydrazino,

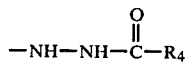

where $R_4$ is $C_1$-$C_8$ alkyl, $C_1$-$C_8$ alkenyl, halo ($C_1$-$C_8$) alkyl, halo ($C_1$-$C_8$) alkenyl, $C_6$-$C_{10}$ cycloalkyl or a group of the formula

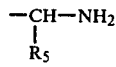

where $R_5$ is H, $C_1$-$C_4$ alkyl or benzyl and the corresponding N-amino carbobenzyloxy derivatives thereof; hydroxy ($C_2$-$C_4$) alkylamino, $C_1$-$C_4$ alkoxy or $C_1$-$C_4$ alkylthio; $R_2$ represents furyl, benzofuryl, phenyl or phenyl substituted with at least one substituent selected from halo (preferably, meta or para-chloro), halo ($C_1$-$C_2$) alkyl, $C_1$-$C_4$ alkoxy (preferably, para-methoxy), methylenedioxy or morpholino when $R_3$ represent hydrogen; or compounds wherein $R_1$ represents hydrazino, $C_1$-$C_4$ alkyl hydrazino, acetyl hydrazino or $C_1$-$C_4$ alkoxy and $R_2$ and $R_3$ are the same and selected from phenyl, substituted phenyl or furyl. As specifically preferred compounds of the foregoing description, there may be mentioned 3-methylhydrazino 5-phenyl-(or 5,6-diphenyl)-1,2,4-triazine, 3-methyl hydrazino-5,6-bis (4'-chlorophenyl)-1,2,4-triazine, 3-trifluoroacetylhydrazino-5-phenyl-1,2,4-triazine, 3-acetylhydrazino-5,6-diphenyl-1,2,4-triazine, 3-hydrazino-5-(3'-trifluoromethyl phenyl)-1,2,4-triazine and 3-methoxy-5-(4'-methoxyphenyl)-1,2,4-triazine.

Additionally, certain of the compounds in accordance with the present invention evidence psychotropic effects, i.e., preferential central nervous system activity including, for example, anti-depressant, muscle relaxant, hypnotic and sedative pharmacoligical properties. Compounds of General Formula I preferred in connection with the compositions and methods of the present invention relative to such central nervous system activity are those wherein $R_1$ represents hydrazino, N-($C_1$-$C_2$ alkyl)-N-(hydroxy $C_1$-$C_4$ alkyl)amino, $C_1$-$C_4$ alkoxy, allyloxy, hydroxy or $C_1$-$C_4$ alkylthio and $R_2$ represents $C_1$-$C_4$ alkyl, phenyl or halo ($C_1$-$C_4$) alkyl phenyl (preferably, trifluoromethyl), when $R_3$ is hydrogen; or wherein $R_1$ is hydroxy, methoxy, allyloxy, hydrazino or methylthio and $R_2$ and $R_3$ are the same and selected from $C_1$-$C_4$ alkyl, phenyl, furyl or pyridyl. Representative of such specifically preferred compounds are 3-hydrazino-5-phenyl-1,2,4-triazine, 3-methylthio-5-t-butyl-1,2,4-triazine and 3-methoxy-5,6-diphenyl-1,2,4-triazine.

While certain of the substituted-1,2,4-triazine compounds set forth hereinabove in Formula I utilized in accordance with the practices of the present invention have heretofore been described without mention of any utility or in connection with utilities different from those described herein, the following compounds of the aforesaid General Formula I are considered novel pharmacologically active compounds wherein correspondingly $R_1$ is hydrazino, $C_1$-$C_4$ alkylhydrazino,

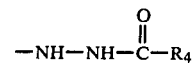

where $R_4$ is $C_1$-$C_8$ alkyl, $C_1$-$C_8$ alkenyl, halo ($C_1$-$C_8$) alkyl, halo ($C_1$-$C_8$) alkenyl, $C_6$-$C_{10}$ cycloalkyl or a group of the formula

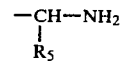

where $R_5$ is H, $C_1$-$C_4$ alkyl or benzyl and the corresponding N-amino carbobenzyloxy derivatives thereof, $C_1$-$C_4$ hydroxyalkylamino, N-($C_1$-$C_2$ alkyl)-N-(hydroxy $C_1$-$C_4$ alkyl amino, $C_1$-$C_4$ alkyl, $C_1$-$C_{10}$ alkoxy, $C_6$-$C_{10}$ aryloxy, $C_3$-$C_6$ cycloalkoxy, phenyl alkoxy, allyloxy, halophenoxy, $C_1$-$C_4$ alkyl phenoxy, $C_1$-$C_4$ alkoxy phenoxy, $C_1$-$C_{10}$ alkylthio, $C_3$-$C_6$ cycloalkylthio, $C_1$-$C_4$ alkyl sulfinyl, $C_1$-$C_4$ alkyl sulfonyl, phenyl $C_1$-$C_4$ alkylthio, dimethylpyrrolidyl or pyridyl; $R_2$ represents hydrogen, $C_1$-$C_4$ alkyl, $C_3$-$C_6$ cycloalkyl, adamantyl, furyl, thienyl, benzofuryl, indolyl, pyridyl, halothienyl or phenyl substituted with at least one substituent selected from halo, $C_1$-$C_6$ alkyl, halo $C_1$-$C_6$ alkyl, $C_1$-$C_6$ alkoxy, acetamido, benzyloxy, diphenyl methyl, morpholino, methylene dioxy or nitro; and $R_3$ represents hydrogen, $C_1$-$C_6$ alkyl, pyridyl, furyl, phenyl or phenyl substituted with at least one substituent selected from halo, $C_1$-$C_6$ alkyl, $C_1$-$C_6$ alkoxy, methylene dioxy or acetamido; subject to the provisos that when $R_2$ is hydrogen, $R_3$ is also hydrogen; when $R_1$ is alkoxy, alkylthio, cycloalkylthio, cycloalkoxy, phenyl alkoxy or hydroxy alkyl amino as defined before, $R_2$ and $R_3$ cannot both be halophenyl, $C_1$-$C_3$ alkyl phenyl or $C_1$-$C_3$ alkoxyphenyl; when $R_1$ is hydroxy, hydrazino, methylthio, methoxy or ethoxy, $R_2$ is other than phenyl and $R_2$ and $R_3$ cannot both be methyl; or when $R_1$ is hydroxy or pyridyl, $R_2$ and $R_3$ cannot both be phenyl; and the pharmaceutically acceptable salts thereof.

In accordance with the practices of the present invention, the active compounds of the invention may be administered alone or in combination with each other or administered in admixture with pharmaceutical diluents, carriers, excipients or adjuvants suitably selected with respect to the intended route of administration and conventional pharmaceutical practices. For example, for oral administration in the form of tablets or capsules, the active compound or compounds of the invention may be combined with such excipients as starch, lactose, sucrose, cellulose, talc, magnesium stearate, acacia, stearic acid and the like. Likewise, appropriate elixirs or suspensions may be formulated with preselected active compounds of the present invention in combination with suitable non-toxic solvents, flavorings, coloring agents, suspending agents and emulsifiers. Similarly, injectable dosage unit forms may be utilized to accomplish intravenous, intramuscular or subcutaneous administration and, for such parenteral administration, suitable sterile aqueous or nonaqueous solutions or suspensions, optionally containing appropriate solutes to effectuate isotonicity, will be employed. Other adjuvants and dosage forms will be apparent to those skilled in the art.

Compounds of the invention or compositions thereof may be administered to warm-blooded animals, i.e., mammals, including, for instance, mice, rats, guinea pigs, dogs and other domesticated animals, or humans. Dosages sufficient to elicit the above-indicated responses, i.e., analgesia, anti-inflammatory, etc., will generally range between about 1 to 300 mg/kg/day in laboratory mice based upon body weight, and preferably, between about 25 to 200 mg/kg/day. The foregoing dosages will normally be administered in three or four divided doses depending upon the desired dosage regimen. Of course, the actual effective dosage to be administered will vary depending upon the specific compound involved as well as the age, weight and responsiveness of the particular animal species under consideration.

The compounds of the invention exhibit relatively low toxicities and the $LD_{50}$ (lethal dose to 50 percent of mice treated intraperitoneally) will generally be greater than 300 mg/kg.

The following non-limiting examples are afforded in order that those skilled in the art may more readily understand the present invention and specific preferred embodiments thereof with respect to the preparation of starting materials, intermediates and compounds in accordance with the foregoing description.

EXAMPLE 1

Preparation of 3-Methylthio-5-phenyl-1,2,4-Triazine

Into a 1000 ml. flask equipped with a magnetic stirrer, heating mantle and condenser were placed S-methylthiosemicarbazide hydrogen iodide (170.1 g, 0.73 m.), 430 ml. ethanol, phenylglyoxal (95.6 g., 0.72 m.) and pyridine (59.2 g, 0.75 m.). The contents were heated at reflux for two hours and the ethanol was recovered under vacuum. The resulting material was extracted with hexane to yield 3-methylthio-5-phenyl-1,2,4-triazine (109.7 g.–74.9%), m.p. 99°–100° C.

Analysis-calculated for $C_{10}H_9N_3S$ (percent): C, 59.09; H, 4.46; N, 20.67. Found (percent): C, 59.58; H, 4.65; N, 20.91.

To minimize formation of the 6-phenyl isomer and further optimize yield of the desired cyclic material phenylglyoxal hydrate can be utilized in lieu of phenylglyoxal in the foregoing synthesis.

EXAMPLE 2

Preparation of 3-methoxy-5-Phenyl-1,2,4-Triazine

Into a 2000 ml. flask equipped with a magnetic stirrer and condenser were placed methanol (1100 ml) and sodium (7.4 g, 0.32 g.atm.). After the sodium reacted, 3-methylthio-5-phenyl-1,2,4-triazine (61.0 g., 0.3 m.) was added and the contents warmed to 40° C. with a hot water bath. After dissolution of the foregoing, the bath was removed and the contents allowed to stir at room temperature for 18 hours. Then $CO_2$ gas was passed into the flask for 30 minutes. The precipitated material was filtered off and discarded. The filtrate was evaporated under vacuum. The remaining material was extracted with chloroform and the chloroform solution evaporated under the vacuum. The remaining material was then extracted with hexane. There was obtained from the hexane solution, 53.5 g (95.3% yield) of 3-methoxy-5-phenyl-1,2,4-triazine, m.p. 73°–74° C.

Analysis-calculated for $C_{10}H_9N_3O$ (percent): C, 64.16; H, 4.85; N, 22.45. Found (percent): C, 63.72; H, 4.90; N, 22.44.

EXAMPLE 3

Preparation of 3-Hydrazino-5-Phenyl-1,2,4-Triazine

Into a 500 ml. flask equipped with a magnetic stirrer, heating mantle and condenser were placed 3-methoxy-5-phenyl-1,2,4-triazine (37.4 g, 0.2 m), 100 ml. of tetrahydrofuran, 95% hydrazine (7.4 g, 0.22 m) and 20 ml. of absolute methanol. The contents were heated at reflux for 3.5 hours and poured into cold water. The precipitated material was filtered off, water washed, air dried and crystallized from 250 ml. of methanol. There was obtained 18.0 g (48.0% yield) of 3-hydrazino-5-phenyl-1,2,4-triazine, m.p. 144°–146° C.

Analysis-calculated for $C_9H_9N_5$ (percent): C, 57.74; H, 4.85; N, 37.41. Found (percent): C, 57.34; H, 4.87; N, 37.17.

EXAMPLE 3A

Preparation of 3-Methylhydrazino-5-Phenyl-1,2,4-Triazine

A solution of 3-methylthio-5-phenyl-1,2,4-triazine (5.0 g, 0.025 m), 10 ml. of methylhydrazine and 100 ml of tetrahydrofuran was placed into a 500 ml flask equipped as before and the contents heated at reflux for 18 hours. 5 ml of additional methylhydrazine was added since thin layer chromatography showed the presence of the 3-methylthio-5-phenyl-1,2,4-triazine starting material. After heating for 2 more hours, the reaction mixture was poured into 300 ml. of ice water. The yellow solid which formed was filtered off, washed with water and air dried. Following recrystallization from 300 ml of heptane, 1.8 g (36% yield) of the title compound was obtained, m.p. 112°–113° C.

Analysis-calculated for $C_{10}H_{11}N_5$ (percent): C, 59.68; H, 5.51; N, 34.81. Found (percent): C, 59.61; H, 5.55; N, 34.86.

EXAMPLE 3B

Preparation of 3-Methylhydrazino-5,6-(4'-Chlorophenyl)-1,2,4-Triazine

Into a 500 ml. round bottom flask was placed 3-methylthio-5,6-di(4'-chlorophenyl)-1,2,4-triazine (10.0 g., 0.03 m.) dissolved in 95% ethanol (300 ml.). To this solution was added methylhydrazine (15 ml.) and the mixture was refluxed for 14 hours, cooled and concentrated. The crude solid was recrystallized from heptane, and then ether resulting in orange-yellow crystals of 3-methylhydrazino-5,6-(4'-chlorophenyl)-1,2,4-triazine, m.p. 147°–148° C.

Analysis-calculated for $C_{16}H_{13}N_5Cl_2$ (percent): C, 55.50; H, 3.78; N, 20.23. Found (percent): C, 55.1; H, 3.6; N, 20.2.

EXAMPLE 3C

Preparation of 3-Acetylhydrazino-5,6-Diphenyl-1,2,4-Triazine

Into a 250 ml. round bottom flask was placed 3-hydrazino-5,6-diphenyl-1,2,4-triazine (10.0 g., 0.04 m.) dissolved in warm dioxane (150 ml.). To this stirring solution was added acetic anhydride (10 ml.) and the mixture was heated to 60° C. for 1 hour. The mixture was cooled, diluted with water and the solid formed was collected and recrystallized from ethyl acetate, and slurried with ether to afford the white solid 3-acetylhydrazino-5,6-diphenyl-1,2,4-triazine, m.p. 166°–168° C.

Analysis-calculated for $C_{17}H_{15}N_5O$ (percent): C, 66.87; H, 4.95; N, 22.94. Found (percent): C, 66.4; H, 4.8; N, 22.7.

EXAMPLE 4

Preparation of 3-Methylthio-5-t-Butyl-1,2,4-Triazine

Into a 1000 ml. flask equipped with a magnetic stirrer, heating mantle and condenser were placed S-methylthio semicarbazide hydrogen iodide (186.4 g, 0.8 m), and 400 ml. of ethanol which were heated to 50° C. A mixture of t-butyl glyoxal (87.8 g, 0.77 m) and pyridine (63.3 g, 0.8 m) was added to the flask over a 10 minute interval. The contents were stirred for 15 minutes and heated at reflux for 1.5 hours, cooled and the ethanol evaporated under vacuum. The resulting material was slurried with 500 ml. of water and the organic fraction extracted with chloroform. The chloroform was evaporated under vacuum and the resulting oil placed in a 300 ml. flask for vacuum distillation. There was obtained 84.8 g (60.0% yield) of 3-methylthio-5-t-butyl-1,2,4-triazine, m.p. 91°–93° C. at 0.1 mm. Hg.

Analysis-calculated for $C_8H_{13}N_3S$ (percent): C, 52.42; H, 7.15; N, 22.93. Found (percent): C, 51.57; H, 7.07; N, 22.69.

EXAMPLE 5

Preparation of 3-Hydrazino-5-t-Butyl-1,2,4-Triazine

Into a 250 ml. flask equipped with a magnetic stirrer, heating mantle and condenser were placed 3-methylthio-5-t-butyl-1,2,4-triazine (18.3 g, 0.1 m), 100 ml. of tetrahydrofuran, 95% hydrazine (3.9 g, 0.11 m) and 10 ml. of absolute methanol. The contents were heated at reflux for 7.5 hours, cooled and the solvents were removed under vacuum. The resulting material was crystallized from 7.5 liters of hexane. There was obtained 14.1 g (84.3% yield) of 3-hydrazino-5-t-butyl-1,2,4-triazine, m.p. 117°–118° C.

Analysis-calculated for $C_7H_{13}N_5$ (percent): C, 50.28; H, 7.84; N, 41.89. Found (percent): C, 49.88; H, 7.73; N, 41.46.

EXAMPLE 6

Preparation of 3-Methylthio-5-(2'-Furyl)-1,2,4-Triazine

Into a 1000 ml. flask equipped as before were placed crude 2-thienyl glyoxal (126 g, 0.9 m), 400 ml. of ethanol, S-methylthiosemicarbazide hydrogen iodide (210 g, 0.9 m) and pyridine (71.2 g, 0.9 m). The contents were heated at reflux for 1 hour, cooled and the ethanol evaporated under vacuum. The resulting material was extracted with 3 liters of hexane. There was obtained 10.3 g (5.5% yield) of 3-methylthio-5-(2'-thienyl)-1,2,4-triazine, m.p. 105°–106° C.

Analysis-calculated for $C_8H_7N_3S_2$ (percent): C, 45.91; H, 3.37; N, 20.08. Found (percent): C, 45.54; H, 3.39; N, 20.05.

EXAMPLE 7

Preparation of 3-Trifluoroacetyl Hydrazino-5-Phenyl-1,2,4-Triazine

To a stirred suspension of 3-hydrazino-5-phenyl-1,2,4-triazine (70 g, 0.374 m) in 1 liter of chloroform was added in portions 70 ml. of trifluoroacetic anhydride at 25° C. to 30° C. controlled by an ice water bath. When the addition was complete, the mixture was heated at 50° C. for 1½ hours. Upon cooling, the resulting precipitated solid was filtered off and dried. This dried solid was slurried with water, filtered, dried and recrystallized from chloroform to yield 60.0 grams (56%) of 3-trifluoroacetyl hydrazino-5-phenyl-1,2,4-triazine as a tan solid, m.p. 193°–194° C.

Analysis-calculated for $C_{11}H_8F_3N_5O$ (percent): C, 46.65; H, 2.85; N, 24.73. Found (percent): C, 46.72; H, 2.76; N, 25.09.

EXAMPLE 8

Preparation of 3-Methoxy-5-(3'-Trifluoromethylphenyl)-1,2,4-Triazine

Into a suitably equipped 500 ml. flask were placed 250 ml. of methanol and sodium (1.4 g, 0.05 g,atm.). Following reaction of the sodium, 10.8 g, 0.04 m 3-methylthio-5-(3'-trifluoromethylphenyl)-1,2,4-triazine (10.8 g, 0.04 m) was added to the flask and the contents allowed to stir at room temperature for 18 hours. Then carbon dioxide gas was passed into the flask for 15 minutes and the precipitated material was filtered off and discarded. The filtrate was evaporated under vacuum and the resulting material extracted with 600 ml. of hexane. There was obtained 9.7 g (63.4% yield) of 3-methoxy-5-(3'-trifluoromethylphenyl)-1,2,4-triazine, m.p. 95°–97° C.

Analysis-calculated for $C_{11}H_8F_3N_3O$ (percent): C, 51.77; H, 3.16; N, 16.47. Found (percent): C, 51.58; H, 3.27; N, 16.28.

EXAMPLE 9

Preparation of 3-Methylthio-5-(2'-Furyl)-1,2,4-Triazine

Into a 1000 ml. flask suitably equipped with a magnetic stirrer, heating mantle and condenser were placed crude 2-furyl glyoxal (111.7 g, 0.9 m), 400 ml. of ethanol, 5-methylthiosemicarbazide hydrogen iodide (210 g, 0.9) and pyridine (71.2 g, 0.9 m). The contents were heated at reflux for 1 hour, cooled and the ethanol evaporated under vacuum. The resulting material was extracted with 3 liters of hexane and there was obtained 20.0 g (11.5% yield) of 3-methylthio-5-(2-furyl)-1,2,4-triazine, m.p. 88°–90° C.

Analysis-calculated for $C_8H_7N_3OS$ (percent): C, 49.72; H, 3.65; N, 21.75. Found (percent): C, 49.40; H, 3.69; N, 21.87.

EXAMPLE 10

Preparation of 3-Methylthio-5,6-Dimethyl-1,2,4-Triazine

Into a suitably equipped 200 ml. flask were placed S-methylthiosemicarbazide hydrogen iodide (222.4 g, 0.954 m), and 700 ml. of ethanol which were heated to 60° C. A mixture of diacetyl (82.1 g, 0.954 m) and pyridine (75.9 g, 0.96 m) was added to the flask over 15 minutes. The contents were heated at reflux for 2 hours and the ethanol distilled off. About 1200 ml. of water was added to the flask and the resulting mixture extracted with chloroform. The chloroform was evaporated under vacuum and the resulting oil was placed in a 200 ml. flask for vacuum distillation. There was obtained 105.5 g (71.2% yield) of 3-methylthio-5,6-dimethyl-1,2,4-triazine, b.p. 100°–102° C. at 0.1 mm Hg.

Analysis-calculated for $C_6H_9N_3S$ (percent): C, 46.42; H, 5.84; N, 27.07. Found (percent): C, 47.03; H, 6.12; N, 26.18.

EXAMPLE 11

Preparation of 3-Allyloxy-5,6-Dimethyl-1,2,4-Triazine

Into a 250 ml. flask equipped as previously described were placed 125 ml. of allyl alcohol and sodium (1.8 g, 0.08 g.atm.). After completion of the sodium reaction, 3-methylthio-5,6-dimethyl-1,2,4-triazine (10.8 g, 0.07 m) was added to the flask and the contents allowed to stir at room temperature for 18 hours. Carbon dioxide gas was passed into the flask for 20 minutes and the contents poured into water. The solution was extracted with chloroform and the chloroform evaporated under vacuum and the resulting material placed in a 50 ml. flask for vacuum distillation. There was obtained 8.5 g (73.5% yield) of 3-allyloxy-5,6-dimethyl-1,2,4-triazine, b.p. 84°–86° C. at 0.08 mm Hg.

Analysis-calculated for $C_8H_{11}N_3O$ (percent): C, 58.16; H, 6.71; N, 25.44. Found (percent): C, 57.05; H, 6.73; N, 25.64.

EXAMPLE 12

Preparation of 3-Methylthio-5,6-(2'-Pyridyl)-1,2,4-Triazine

To a solution of S-methylthiosemicarbazide hydrogen iodide (23 g, 0.1 m) dissolved in ice water (200 ml.) was added a solution of 2,2'-pyridil (21 g, 0.1 m) and sodium bicarbonate (9 g, 0.11 m) in 50% ethanol (250 ml.). Upon addition, gas was evolved and addition was carried out slowly while cooling. When gas evolution ceased, the mixture was stirred for 15 hours at room temperature. The mixture was diluted with about 200 ml. of water and repeatedly extracted with chloroform. The chloroform extracts were dried over anhydrous magnesium sulfate and concentrated to give a yellow solid which was recrystallized from hexane to yield 3-methylthio-5,6-(2'-pyridyl)-1,2,4-triazine (85%), m.p. 122°–123° C.

Analysis-calculated for $C_{14}H_{11}N_5S$ (percent): C, 59.79; H, 3.91; N, 24.91. Found (percent): C, 59.57; H, 3.90; N, 25.35.

EXAMPLE 13

Preparation of 3-Methylthio-5-(3'-Indolyl)-1,2,4-Triazine

Into a suitably equipped 1000 ml. flask were placed a solution of 3'-indolyl glyoxal (27.0 g, 0.15 m) dissolved in 200 ml of ethanol and sodium bicarbonate (13.2 g, 0.157 m) dissolved in 50 ml. of water to which was added a solution of S-methylthiosemicarbazide hydrogen iodide (36.5 g, 0.157 m) dissolved in 50 ml. of water. The mixture was then heated at reflux for about 48 hours. Following reflux, the mixture was poured into ice water and the resulting solid was recrystallized twice from acetone. This solid was then slurried with water, filtered off and dried to yield 2.7 g of 3-methylthio-5-(3'-indolyl)-1,2,4-triazine, m.p. 232°–234° C.

Analysis-calculated for $C_{12}H_{10}N_4S$ (percent): C. 59.48; H, 4.16, N, 23.12. Found (percent): C, 59.23; H, 4.17; N, 23.49.

EXAMPLE 14

Preparation of 3-Methylthio-5,6-(4'-Acetamido Phenyl)-1,2,4-Triazine

Into a 100 ml flask was placed p-acetamidobenzil (10 g, 0.0285 m) dissolved in dimethylformamide (50 ml) and to this solution was added an aqueous solution of $NaHCO_3$ (1.0 g) and S-methylthiosemicarbazide hydrogen iodide (7 g, 0.03 m). The mixture was stirred at room temperature for 15 hours, then heated on a steam bath for 1 hour, cooled and the precipitate which formed was collected and washed with $H_2O$, acetone, dried under reduced pressure to give 3-methylthio-5,6-(4'-acetamidophenyl)-1,2,4-triazine (70% yield), m.p. 300° C.

Analysis-calculated for $C_{20}H_{19}N_5O_2S$ (percent): C, 61.07; H, 4.83; N, 17.27. Found (percent): C, 60.69; H, 4.95; N, 17.76.

EXAMPLE 15

Preparation of 3-Methylthio-5-(3'-Chlorophenyl)-1,2,4-Triazine

Into a suitably equipped 500 ml. flask were placed selenium dioxide (34.4 g, 0.31 m), 250 ml. of dioxane and 10 ml. of water. The contents were heated to 60° C. and 3'-chloroacetophenone (46.4 g, 0.3 m) was added in one portion. The contents were heated at reflux for 2 hours, cooled and filtered. The solvents were removed under vacuum. The resulting 2-(3'-chlorophenyl) glyoxal was dissolved in 100 ml. of ethanol and additional selenium was filtered off.

Into a second 500 ml. flask were placed the crude 2-(3'-chlorophenyl) glyoxal (50.6 g, 0.3 m) thus obtained in 100 ml. of ethanol, pyridine (24.0 g, 0.3 m) and S-methylthiosemicarbazide hydrogen iodide (70. g, 0.3 m). The contents were heated at reflux for 1 hour and cooled. The precipitated material was filtered off and extracted with 1200 ml. of hexane. The hexane was evaporated off and the resulting material crystallized from methanol (200 ml.). There was obtained 26.0 g (36.5% yield) of 3-methylthio-5-(3'-chlorophenyl)-1,2,4-triazine, m.p. 79°–81° C.

Analysis-calculated for $C_{10}H_8ClN_3S$ (percent): C, 50.52; H, 3.39; N, 17.68. Found (percent): C, 50.70; H, 3.32; N, 17.64.

EXAMPLE 16

Preparation of 3-Methylthio-5,6-Bis(3',4'-Methylene Dioxy-Phenyl)-1,2,3-Triazine Into a 100 ml. round-bottomed flask was placed 3,4-methylene dioxy benzil (5 g, 0.016 m) dissolved in ethanol-dimethylformamide. To this solution was added S-methylthiosemicarbazide hydrogen iodide (4.0 g, 0.18 m) and sodium bicarbonate (2.0 g, 0.2 m). After gas evolution had ceased, the mixture was refluxed with stirring for 4 hours. Upon cooling, a yellow solid formed which was collected, washed repeatedly with acetone and ether, and dried under reduced pressure to yield 3-methylthio-5,6-bis(3',4'-methylene dioxyphenyl)-1,2,4-triazine (80% yield), m.p. 207°–209° C.

Analysis-calculated for $C_{18}H_{13}N_3O_4S$ (percent): C, 58.86; H, 3.54; N, 11.44. Found (percent): C, 58.80; H, 3.57; N, 11.31.

EXAMPLES 17–11

The following compounds were prepared using the foregoing synthesis procedures with appropriate selection of the substituted glyoxal reactant for condensation with S-methylthiosemicarbazide hydrogen iodide and conversion of the resulting 3-methylthio-1,2,4-triazine derivative or, where appropriate, by selection of a substituted alpha beta diketone for condensation with semicarbazide, cyclization and chlorination to obtain the 3-chloro-1,2,4-triazine derivative for conversion into the desired 3-substituted-5-mono or 5,6-disubstituted-1,2,4-triazines.

Example 17—3-methoxy-5-methyl-1,2,4-triazine, m.p. 87°–89° C.

Example 18—3-methoxy-5-t-butyl-1,2,4-triazine, m.p. 45°–46° C.

Example 19—3-methylthio-5-(3'-trifluoromethyl phenyl)-1,2,4-triazine, m.p. 123°–125° C.

Example 20—3-methoxy-5-(2'-furyl)-1,2,4-triazine, m.p. 96°–97° C.

Example 21—3-ethoxy-5-phenyl-1,2,4-triazine, m.p. 48°–49° C.

Example 22—3-methoxy-5-(2'-naphthyl)-1,2,4-triazine, m.p. 130°–131° C.

Example 23—3-methoxy-5,6-dimethyl-1,2,4-triazine, b.p. 55°–57° C. at 0.05 mm Hg.

Example 24—3-isopropoxy-5,6-dimethyl-1,2,4-triazine, b.p. 75°–78° C. at 0.5 mm Hg.

Example 25—3-hydrazino-5,6-dimethyl-1,2,4-triazine, m.p. 126°–127° C.

Example 26—3-methoxy-5,6-di(4'-methylphenoxy)-1,2,4-triazine, m.p. 128°–129° C.

Example 27—3-methoxy-5,6-di(2'-pyridyl)-1,2,4-triazine, m.p. 132°–133° C.

Example 28—3-B-hydroxyethyl amino-5-phenyl-1,2,4-triazine, m.p. 152°–153° C.

Example 29—3-methoxy-5-(1'-naphthyl)-1,2,4-triazine, m.p. 76°–77° C.

Example 30—3-methoxy-5-(2'-naphthyl)-1,2,4-triazine, m.p. 130°–131° C.

Example 31—3-n-propoxy-5-phenyl-1,2,4-triazine, m.p. 44°–45° C.

Example 32—3-methylthio-5-(3'-methoxy-4'-hydroxyphenyl)-1,2,4-triazine, m.p. 190°–191.5° C.

Example 33—3-methylthio-5-(3',4'-dimethoxyphenyl)-1,2,4-triazine, m.p. 148°–151° C.

Example 34—3-methylthio-5-(1'-adamantyl)-1,2,4-triazine, m.p. 140°–141° C.

Example 35—3-methylthio-5-(2'-benzofuryl)-1,2,4-triazine, m.p. 134°–135° C.

Example 36—3-methoxy-5-(1'-adamantyl)-1,2,4-triazine, m.p. 101°–102° C.

Example 37—3-methylthio-5-cyclopropyl-1,2,4-triazine, m.p. 44°–46° C.

Example 38—3-methoxy-5-(3',4'-dimethoxyphenyl)-1,2,4-triazine, m.p. 167°–169° C.

Example 39—3-methylthio-5-(2',4',6'-trimethylphenyl)-1,2,4-triazine, m.p. 97°–98° C.

Example 40—3-methylthio-5-(4'-morpholino phenyl)-1,2,4-triazine, m.p. 127°–128° C.

Example 41—3-methoxy-5-cyclopropyl-1,2,4-triazine, b.p. 119°–121° C. at 1.8–2.1 mm Hg.

Example 42—3-methylthio-5-(2',4'-difluorophenyl)-1,2,4-triazine, m.p. 79°–80° C.

Example 43—3-methylthio-5-(4'-bromophenyl)-1,2,4-triazine, m.p. 153°–154° C.

Example 44—3-methylthio-5-(4'-methoxyphenyl)-1,2,4-triazine, m.p. 118°–119° C.

Example 45—3-methoxy-5-(4'-bromophenyl)-1,2,4-triazine, m.p. 108°–109° C.

Example 46—3-methoxy-5-(4'-methoxyphenyl)-1,2,4-triazine, m.p. 106°–107° C.

Example 47—3-allyloxy-5-phenyl-1,2,4-triazine, b.p. 155° C. at 0.3 mm Hg.

Example 48—3-methoxy-5,6-diphenyl-1,2,4-triazine, m.p. 78°–79° C.

Example 49—No Example.

Example 50—3-(N-methyl-N-(B-hydroxyethyl)amino)-5,6-bis-(4'-methoxyphenyl)-1,2,4-triazine, m.p. 108°–110° C.

Example 51—3-chloro-5,6-diphenyl-1,2,4-triazine, m.p. 152°–155° C.

Example 52—3-(cis-2',5'-dimethyl pyrrolidyl)-5,6-diphenyl-1,2,4-triazine, m.p. 131°–134° C.

Example 53—3-phenoxy-5,6-diphenyl-1,2,4-triazine, m.p. 123°–125° C.

Example 54—3-methylthio-5,6-bis(4'-chlorophenyl)-1,2,4-triazine, m.p. 142°–143° C.

Example 55—3-(N-methyl-N-B-hydroxyethyl amino)-5,6-diphenyl-1,2,4-triazine, m.p. 101°–104° C.

Example 56—3-benzylthio-5,6-dimethyl-1,2,4-triazine, m.p. 47°–48° C.

Example 57—3-methylthio-5-(4'-nitrophenyl)-1,2,4-triazine, m.p. 218°–219° C.

Example 58—3-methoxy-5-(2',4'-difluorophenyl)-1,2,4-triazine, m.p. 91°–93° C.

Example 59—3-methylthio-5-phenyl-1,2,4-triazine (hydrogen iodide salt), m.p. 191°–192° C.

Example 60—3-(4'-methylphenoxy)-5,6-diphenyl-1,2,4-triazine, m.p. 154°–157° C.

Example 61—3-ethoxy-5,6-diphenyl-1,2,4-triazine, m.p. 73°–74° C.

Example 62—3-methylthio-5-(4'-ethylphenyl)-1,2,4-triazine, m.p. 71°–72° C.

Example 63—3-(4'-methoxyphenoxy)-5-phenyl-1,2,4-triazine, m.p. 149°–151° C.

Example 64—3-n-pentoxy-5-phenyl-1,2,4-triazine, m.p. 36°–38° C.

Example 65—3-n-butoxy-1,2,4-triazine, b.p. 129°–138° at 13 mm Hg.

Example 66—3-methoxy-5-(2'-thienyl)-1,2,4-triazine, m.p. 129°–130° C.

Example 67—3-hydrazino-5-(3'-trifluoromethylphenyl)-1,2,4-triazine, m.p. 140°–142° C.

Example 68—3-methylthio-5-(3'-methoxyphenyl)-1,2,4-triazine, m.p. 96°–97° C.

Example 69—3-methoxy-5-(3'-methoxyphenyl)-1,2,4-triazine, m.p. 106°–107° C.

Example 70—3-methylthio-5-(5'-chloro-2'-thienyl)-1,2,4-triazine, m.p. 149°–150° C.

Example 71—3-methylthio-5-(1'-naphthyl)-1,2,4-triazine, m.p. 116.5°–118° C.

Example 72—3-methylthio-(4'-methylphenyl)-1,2,4-triazine, m.p. 160°–161° C.

Example 73—3-(N-methyl-N-(B-hydroxyethyl)amino-5-phenyl-1,2,4-triazine, m.p. 90°–91° C.

Example 74 - 3-methylthio-5-(4'-chlorophenyl)-1,2,4-triazine, m.p. 165°–166° C.

Example 75 - 3-methoxy-5-(3'-chlorophenyl)-1,2,4-triazine, m.p. 93°–94° C.

Example 76 - 3-methylthio-5,6-bis-(2'-furyl)-1,2,4-triazine, m.p. 92°–92° C.

Example 77 - 3-hydrazino-5,6-bis-(2'-furyl)-1,2,4-triazine, m.p. 168°–169° C.

Example 78 - 3-methyl-5,6-bis-(4'-methylphenyl)-1,2,4-triazine, m.p. 166°–167° C.

Example 79 - 3-methylsulfonyl-5,6-dimethyl-1,2,4-triazine, m.p. 97°–98° C.

Example 80 - 3-methylthio-5,6-bis(3',4'-dimethoxyphenyl)-1,2,4-triazine, m.p. 130°–131° C.

Example 81 - 3-(2'-pyridyl)-5,6-diphenyl-1,2,4-triazine, m.p. 191°–193° C.

Example 82 - 3-methoxy-6-phenyl-1,2,4-triazine, m.p. 94°–95° C.

Example 83 - 3-methylthio-5-(3'-methoxy-4'-benzyloxyphenyl)-1,2,4-triazine, m.p. 158°-159° C.

Example 84 - 3-methylthio-5-(9'-anthracenyl)-1,2,4-triazine, m.p. 181°-184° C.

Example 85 - 3-methoxy-5-(9'-anthracenyl)-1,2,4-triazine, m.p. 195°-195° C.

Example 86 - 3-methylthio-5-(3',4'-methylene dioxyphenyl)-1,2,4-triazine, m.p. 166°-167° C.

Example 87 - 3-methylthio-5-diphenylmethyl-1,2,4-triazine, m.p. 162°-163° C.

Example 88 - 3-methylthio-5-(4'-ethoxyphenyl)-1,2,4-triazine, m.p. 119°-120° C.

Example 89 - 3-methoxy-5-(2',4',6'-trimethylphenyl)-1,2,4-triazine, m.p. 96°-97° C.

Example 90 - 3-hydroxy-5-phenyl-1,2,4-triazine, m.p. 235°-237° C.

Example 91 - 3-methoxy-5-(4'-methoxyphenyl)-1,2,4-triazine, m.p. 106°-107° C.

Example 92 - 3-methoxy-5,6-bis(3',4'-dimethoxyphenyl)-1,2,4-triazine, m.p. 83°-84° C.

Example 93 - 3-methylthio-5,6-bis(4'-methoxyphenyl)-1,2,4-triazine, m.p. 152°-153° C.

Example 94 No Example

Example 95 - 3-isopropoxy-5,6-diphenyl-1,2,4-triazine, m.p. 96°-98° C.

Example 96 - 3-methoxy-5,6-bis(4'-chlorophenyl)-1,2,4-triazine, m.p. 146°-147° C.

Example 97 - No Example

Example 98 - 3-methoxy-5-(4'-chlorophenyl)-1,2,4-triazine, m.p. 131°-133° C.

Example 99 No Example

Example 100 - 3-methoxy-5-(2'-benzofuryl)-1,2,4-triazine, m.p. 139°-140° C.

Example 101 - 3-methoxy-5-(3',4'-methylene dioxyphenyl)-1,2,4-triazine, m.p. 129°-130° C.

Example 102 - 3-methoxy-5-(4'-morpholinophenyl)-1,2,4-triazine, m.p. 122°-123° C.

Example 103 - 3-methylthio-5-(2'-chlorophenyl)-1,2,4-triazine, m.p. 68°-69° C.

Example 104 - 3-methoxy-5,6-bis(2'-furyl)-1,2,4-triazine, m.p. 105°-107° C.

Example 105 - 3-methoxy-5-phenyl-6-methyl-1,2,4-triazine, m.p. 72°-74° C.

Example 106 - 3-n-nonylthio-5-phenyl-1,2,4-triazine, m.p. 47°-49° C.

Example 107 - 3-adamantanoyl hydrazino-5-phenyl-1,2,4-triazine, m.p. 218°-220° C.

Example 108 - 3-propionylhydrazino-5-(4'-chlorophenyl)-1,2,4-triazine, m.p. 213°-214° C.

Example 109 - 3-acetylhydrazino-5-phenyl-1,2,4-triazine, m.p. 181°-183° C.

Example 110 - 3-cyclohexanoylhdyrazino-5-phenyl-1,2,4-triazine, m.p. 208°-209° C.

Example 111 - 3-hexanoylhydrazino-5-phenyl-1,2,4-triazine, m.p. 198°-200° C.

The following examples further illustrate the preparation of carbobenzyloxy N-protected α-aminoacylhydrazino and α-aminoacylhydrazino derivatives of the present invention.

EXAMPLE 112

Preparation of Glycine-N-Carbobenzyloxy-2-(5-Phenyl-1,2,4-Triazin-3-yl)-Hydrazide Carbobenzyloxy glycine (2.1 g., 0.01 m.) was dissolved in pyridine (dried over Ba O) and chilled to −10° C. under inert atmosphere. Dicyclohexyl-carbodiimide (2.1 g., 0.01 m.) was dissolved in warm pyridine and added by syringe. 3-Hydrazino-5-phenyl-1,2,4-triazin (1.9 g., 0.01 m.) was dissolved in pyridine and added dropwise by syringe to the stirring mixture at −10° C. The ice bath was removed and the mixture allowed to stir at room temperature for 5 hours. The precipitate which formed was removed by filtration and identified as dicyclohexyl urea and discarded. The solution was concentrated and the viscous oil taken up in hot ethyl acetate. Addition of small amounts of pet. ether and cooling resulted in the formation of the title compound as a yellow powder, m.p. 166°-167° C.

Analysis-calculated for $C_{19}H_{18}N_6O_3$ (percent): C, 60,82; H, 4.77; N, 22.22. Found (percent): C, 61.05; H, 5.25; N, 21.91.

EXAMPLE 113

Preparation of $N_2$-(5-Phenyl-1,2,4-Triazin-3-yl) Glycine Hydrazide (Dihydrobromide Hydrate)

Into 500 ml. erlenmeyer flask was placed glycine-N-carbobenzyloxy-2-(5-phenyl-1,2,4-triazin-3-yl)-hydrazide (16.0 g., 0.045 m.) dissolved in glacial acetic acid (100 ml.). To this solution was added 100 ml. of 4 N HBr/AcOH and the flask stored for 1 hour at room temperature with intermittent stirring. The reaction mixture was diluted with excess anhydrous ether (300 ml.) and stored at 5° C. for 12 hours, forming a red solid which was collected and slurried in ether several times. Upon drying in a vacuum oven for 10 hours, the title compound was recovered as a pale yellow solid, m.p. 220°-221° C. Analysis-calculated for $C_{11}H_{12}N_6O$ . 2 HBr . $H_2O$ (percent): C, 31.13; H, 3.77; N, 19.81. Found (percent): C, 31.1; H, 3,9: N, 20.1.

The following compounds were similarly prepared using the foregoing synthesis methods with appropriate selection of the N-carbobenzyloxy amino acid reactant and cleavage of the N-protecting group.

Example 114 - $N_2$-(5-p-chlorophenyl-1,2,4-triazin-3-yl) alanine hydrazide (dihydrobromide hydrate), m.p. 252°-254° C.

Example 115 - $N_2$-(5-phenyl-1,2,4-triazin-3-yl) valine hydrazide (dihydrobromide hydrate), m.p. 274°-275° C.

Example 116 - $N_2$-(5-phenyl-1,2,4-triazin-3-yl) phenylalanine hydrazide (dihydrobromide hydrate), m.p. 264°-265° C.

PHARMACOLOGICAL ACTIVITY

The results of studies demonstrating the indicated anti-inflammatory, analgesic, hypotensive and central nervous system effects observed upon administration of effective dosages of typical preferred compounds in accordance with the present invention and the procedures utilized to evaluate pharmacological activity are set forth below.

A. Anti-inflammatory Assay

Anti-inflammatory activity, i.e., effectiveness in the prevention and inhibition of granuloma tissue formation, is demonstrated by relative inhibition of carrageenin-induced edema as determined by the diminution of experimental edema induced in the hind paw of a rat by the injection of carrageenin. The procedure employed is a modification of the method of Winter et al, Proc. Soc. Exptl. Biol. Med. 111:544 (1962). The device used for measurement of the paw volume is an adaptation of the water displacement procedure described by Adamkiewicz et al, Can. J. Biochem. Physiol. 33:332 (1955). Test compounds were administered orally, one hour prior to the intraplantar injection of 0.05 ml. of sterile 1.0 percent solution of carrageenin into the left hind paw of male rats (Long Evans strain) weighing between about 130–200 grams. At peak swelling time (3 hours) the volume of edema was calculated by differential paw volumes.

Table I sets forth the results obtained (indicated as percent reduction of edema compared to phenylbutazone control values) at the indicated dosages for each of the identified compounds.

TABLE I

| Carragenin Assay | | |
|---|---|---|
| Compound Example No. | Dose (mg/kg) | % Reduction of Edema |
| 1 | 175 | 27 |
| 2 | 200 | 86 |
| 3 | 40 | 55 |
| 3A | 100 | 76 |
| 4 | 150 | 57 |
| 5 | 175 | 82 |
| 6 | 200 | 51 |
| 7 | 150 | 41 |
| 8 | 100 | 77 |
| 9 | 200 | 39 |
| 10 | 70 | 54 |
| 11 | 200 | 63 |
| 12 | 200 | 19 |
| 13 | 200 | 71 |
| 14 | 200 | 12 |
| 17 | 200 | 8 |
| 18 | 200 | 64 |
| 19 | 200 | 51 |
| 20 | 175 | 70 |
| 21 | 200 | 96 |
| 22 | 200 | 7 |
| 23 | 40 | 4 |
| 24 | 200 | 37 |
| 25 | 40 | 46 |
| 26 | 200 | 12 |
| 27 | 200 | 46 |
| 28 | 200 | 43 |
| 29 | 200 | 22 |
| 30 | 200 | 7 |
| 31 | 200 | 51 |
| 32 | 200 | 5 |
| 33 | 200 | 32 |
| 34 | 200 | 17 |
| 35 | 200 | 2 |
| 36 | 150 | 30 |
| 37 | 200 | 86 |
| 38 | 200 | 52 |
| 39 | 200 | 7 |
| 40 | 200 | 19 |
| 41 | 200 | 57 |
| 42 | 150 | 10 |
| 43 | 200 | 20 |
| 44 | 200 | 18 |
| 45 | 200 | 33 |
| 46 | 200 | 17 |
| 47 | 200 | 67 |
| 48 | 200 | 17 |
| 50[1] | 200 | 67 |
| 51 | 200 | 4 |
| 52 | 200 | 22 |
| 53 | 200 | 7 |
| 54 | 200 | 7 |
| 55 | 200 | 23 |
| 56 | 200 | 52 |
| 57 | 200 | 16 |
| 58 | 150 | 36 |
| 59 | 150 | 14 |
| 60 | 200 | 18 |
| 61 | 200 | 12 |
| 62 | 200 | 33 |
| 63 | 200 | 15 |
| 64 | 200 | 29 |
| 108 | 100 | 40 |

TABLE I-continued

| Carragenin Assay | | |
|---|---|---|
| Compound Example No. | Dose (mg/kg) | % Reduction of Edema |
| 113 | 50 | 32 |

B. Analgesic Assay

The phenylquinone writhing test was employed to evaluate analgesic activity according to the following procedure:

Phenylquinone (phenyl-p-benzoquinone, No. 7104, Eastman Organic Chemicals) is made up as a 0.02% aqueous solution in 5% ethyl alcohol. Phenylquinone solutions are made up fresh twice daily. Standard reference agents and the test compounds are dissolved or suspended in a 0.25% methylcellulose solution. A control group consisting of ten mice (Carworth $CF_1$ male mice) are administered the 0.02% phenylquinone solution at a dose of 0.25 ml/mouse. The mice are housed individually and observed closely for ten minutes for exhibition of writhing. The onset of writhing occurs within three minutes and 100% of the mice must writhe within ten minutes. Test compounds are administered orally to groups of ten mice. The volume given is 0.01 ml/gram of body weight. Activity can be studied at 15, 30, 60, and 120 minutes after oral administration. After the designated time interval of a dose group has elapsed, the mice are challenged with phenylquinone intraperitoneally. Complete blocking of the writhing syndrom for the ten minute observation period in any one mouse is considered a positive analgesic response for that mouse. Conversely, if any mouse writhes definitely once it is considered not to be protected. The number of mice not writhing in group multiplied by ten equals percent analgesia for that dose at that time interval.

The compounds tested, dose administered, and analgesic response are summarized in Table II.

TABLE II

| Phenylquinone Writhing Assay (% Control) | | | | |
|---|---|---|---|---|
| Compound Example No. | Dose (mg/kg) | 15 Min. | 30 Min. | 60 Min |
| 1 | 50 | 10 | —[1] | — |
|  | 100 | — | 10 | — |
| 2 | 12.5 | 10 | 30 | 30 |
|  | 25 | 40 | 60 | 50 |
|  | 50 | 90 | 80 | 70 |
| 3 | 30 | — | 30 | — |
|  | 70 | — | 90 | — |
|  | 100 | 100 | — | — |
| 3A | 100 | 60 | 30 | 30 |
| 4 | 100 | — | 20 | — |
| 5 | 25 | — | 20 | — |
| 6 | 25 | 20 | — | — |
|  | 50 | — | 70 | — |
|  | 100 | — | 10 | — |
|  | 100 | — | 50 | — |
| 7 | 15 | 50 | — | 10 |
| 8 | 70 | — | 10 | — |
| 9 | 50 | — | 50 | 10 |
| 10 | 100 | — | 70 | 20 |
| 11 | 100 | — | 30 | — |
| 12 | 100 | — | 10 | 20 |
| 15 | 60 | 10 | — | — |
| 18 | 50 | — | 40 | — |
| 19 | 30 | — | 20 | — |
| 20 | 30 | — | 10 | — |
| 22 | 100 | 20 | 10 | 10 |
| 24 | 70 | — | 10 | — |

TABLE II-continued

Phenylquinone Writhing Assay (% Control)

| Compound Example No. | Dose (mg/kg) | 15 Min. | 30 Min. | 60 Min |
|---|---|---|---|---|
| 25 | 10 | 20 | 10 | — |
|  | 12.5 | — | 20 | — |
|  | 25 | — | 90 | — |
| 26 | 25 | 10 | 10 | 10 |
|  | 50 | 40 | 10 | 20 |
|  | 100 | 20 | 50 | 50 |
| 28 | 100 | 30 | 10 | 10 |
| 29 | 30 | 10 | — | — |
|  | 100 | 10 | — | — |
|  | 50 | — | 10 | — |
| 31 | 100 | 10 | — | — |
| 32 | 100 | 30 | 10 | 10 |
| 34 | 100 | 30 | 10 | — |
| 35 | 100 | 10 | 10 | 10 |
| 37 | 100 | 20 | — | — |
| 38 | 100 | — | 20 | 10 |
| 39 | 100 | 10 | — | 10 |
| 40 | 100 | 30 | 10 | — |
| 42 | 100 | 20 | 10 | — |
| 43 | 100 | 10 | 10 | 10 |
| 44 | 100 | 10 | 10 | 20 |
| 50 | 25 | 30 | 40 | 20 |
|  | 50 | 60 | 50 | 40 |
|  | 100 | 70 | 100 | 80 |
| 52 | 100 | — | 30 | 10 |
| 53 | 100 | 20 | — | 10 |
| 54 | 100 | 10 | — | — |
| 55 | 100 | 20 | — | — |
| 65 | 50 | — | 10 | — |
| 66 | 25 | 20 | 10 | — |
|  | 50 | 80 | 50 | 20 |
|  | 60 | 100 | 80 | 40 |
| 67 | 25 | — | 20 | 10 |
|  | 50 | 70 | 30 | 30 |
|  | 100 | 10 | 60 | 40 |
| 68 | 30 | 10 | — | — |
| 69 | 50 | 10 | 20 | 20 |
|  | 100 | 10 | 20 | 10 |
| 70 | 50 | 10 | 20 | 10 |
|  | 100 | 10 | 20 | 10 |
| 71 | 100 | — | 10 | 20 |
| 72 | 100 | 20 | — | — |
| 73 | 100 | 10 | — | — |
| 74 | 100 | 10 | — | — |
| 75 | 60 | 100 | 90 | 70 |
| 76 | 30 | 10 | — | — |
| 77 | 25 | 20 | 20 | 20 |
|  | 75 | 20 | 10 | 10 |
| 78[2] | 50 | 20 | 20 | 20 |
|  | 100 | 50 | 80 | 50 |
| 79 | 100 | — | 30 | 30 |
| 80 | 100 | 10 | 10 | — |
| 81 | 100 | 10 | 20 | — |
| 82 | 25 | 10 | — | — |
|  | 50 | 10 | 10 | — |
| 83 | 100 | 10 | — | — |
| 84 | 100 | — | 10 | 20 |
| 85 | 100 | 10 | — | — |
| 86 | 100 | 20 | — | — |
| 87 | 100 | 10 | — | 10 |
| 88 | 100 | 10 | — | — |
| 89 | 100 | 10 | — | 10 |
| 90 | 100 | — | — | 20 |
| 91 | 100 | 30 | 10 | — |
| 92 | 100 | 10 | 10 | — |
| 93 | 100 | 20 | 30 | 30 |
| 94 | 100 | — | 10 | — |
| 95 | 100 | 10 | 10 | 20 |
| 96 | 100 | — | 30 | 10 |
| 97 | 100 | 40 | 20 | — |
| 108 | 25 | 30 | 50 | 50 |
| 114 | 50 | 50 | 50 | 60 |
| 116 | 100 | 30 | 60 | 60 |

[1] Indicates not tested at indicated time interval
[2] See Belgium Pat. No. 839,469

C. Anti-Hypertensive Assay

Spontaneously hypertensive rats, 12 to 16 weeks of age, were used in this assay. Systolic blood pressures were determined by the tail cuff method, utilizing capacitance transducers for the detection of pressure, an aneroid manometer for measuring pressure, and an oscilloscope for visualizing the disappearance and/or appearance of the pressure pulse. Heart rate was measured by a biotachometer. Groups of five rats having systolic blood pressures of 170 mmHg or greater were chosen and the test compounds administered at the doses indicated below (oral) as a solution or suspension in 0.25% methylcellulose (MC) at a volume of 5 ml/kg. One group served as the control and received the vehicle. Twenty-four hours after dosing, systolic blood pressure and heart rate were recorded. A second dose of compound was administered and blood pressure and heart rate determined at 4 and 24 hours after the second dose.

The results observed are set forth in Table III below:

TABLE III

SHR Assay

| Compound Example No. | Dose (mg/hg) | Mean Drop - mm/Hg. | | | | | |
|---|---|---|---|---|---|---|---|
|  |  | 4 hr. | 24 hr. | 4 hr. | 24 hr | 28 hr. | 48 hr. |
| 3 | 50 | 30 | 43 | 58 | 60 | — | — |
| 3A | 100 | 0 | 49 | 56 | 92 |  |  |
| 3B | 100 | 0 | 41 | 48 | 73 |  |  |
| 3C | 100 | 55 | 70 | — | 90 |  |  |
| 7 | 50 | 0 | 25 | 56 | 59 |  |  |
|  | 100 | 51 | 29 | 70 | 88 | 63 | 45 |
| 20 | 100 | 30 | 0 | 54 | 38 |  |  |
| 28 | 100 | 10 | 2 | 10 | 2 | — | — |
| 41 | 100 | 28 | 9 | 1 | 8 | — | — |
| 46 | 100 | 17 | 22 | 12 | 19 | — | — |
| 61 | 100 | 2 | 4 | 18 | 11 |  |  |
| 67 | 100 | 26 | 0 | 48 | 40 |  |  |
| 78 | 100 | 8 | +5 | 11 | 12 |  |  |
| 98 | 100 | 0 | 0 | 37 | 29 | — | — |
| 99 | 100 | +8 | 16 | 11 | 19 | — | — |
| 100 | 50 | +1 | 0 | 0 | 11 | — | — |
| 101 | 50 | 3 | 7 | 9 | 3 | — | — |
| 102 | 100 | 11 | 4 | 7 | 12 | — | — |
| 103 | 100 | 2 | 10 | 10 | 13 | — | — |
| 107 | 100 | 49 | 86 | 41 | 36 |  |  |

TABLE III-continued

SHR Assay

| Compound Example No. | Dose (mg/hg) | Mean Drop - mm/Hg. | | | | |
|---|---|---|---|---|---|---|
| | | 4 hr. | 24 hr. | 4 hr. | 24 hr | 28 hr. · 48 hr. |
| 108 | 100 | 47 | 79 | 107 | 111 | |
| 109 | 100 | 40 | 94 | 106 | 104 | |
| 111 | 100 | 53 | 53 | 81 | 68 | |
| 112 | 100 | 32 | 37 | 47 | 36 | |
| 113 | 50 | 41 | 35 | 105 | 91 | |
| 114 | 100 | 44 | 58 | 91 | 103 | |
| 115 | 100 | 23 | 17 | 37 | 44 | |
| 116 | 100 | 26 | 38 | 75 | 82 | |

D. Psychotropic Effects

The central nervous system activity of certain of the preferred compounds in accordance with the present invention were determined using the following neuropharmacological profile assay procedures.

White male mice of the Carworth Farm Strain (CF-1) weighing 18–22 grams were used in these determinations. The test compound, regardless of solubility, is suspended in a 0.25% aqueous methylcellulose solution. Intraperitoneal injections were administered in logarithmic progression and sequentially. The dose levels employed routinely are 10, 30, 100, and 300 mg/kg, using four male mice at each dose level. Since this test was conducted in a sequential manner, the first dose administered was at 300 mg/kg. The mice were injected at this dose level and observed for gross changes produced by the drug, such as behavioral, neurological, autonomic, and toxic effects.

The animals were observed continuously for one hour and if no signs of pharmacological or toxicological activity were present at the end of the first hour, they were intermittently checked for activity every fifteen minutes thereafter for two consecutive hours. At the end of the third hour of observation, if no demonstrable change had occurred in the behavior of the mice, the compound was conditionally considered inactive and the animals were checked intermittently for forty-eight hours. Subsequent dose levels below 300 mg/kg were not administered in this case. Alternatively, if demonstrable pharmacological changes occurred within the first three hours after administration of the drug at 300 mg/kg, the subsequent doses were administered and the animals observed for changes in overt behavior. The observation period begins immediately following the injection and the animals are then continuously observed for three hours and intermittently checked thereafter for forty-eight hours. The animals were observed and signs and symptoms of pharmacological activity were recorded continuously until no further symptoms developed and until the symptoms that had appeared were no longer present. The animals were observed in a fixed environment consisting of a 15 inch square in which their movements were not restricted. It was very important that the animals were free to move about for evaluation of spacial orientation, alertness, and spontaneous motor activity. The animals were systematically observed and manipulated to measure the onset, peak effect, duration and character of drug action.

The major characteristics observed relative to central nervous system activity for the compounds indicated are summarized in the following Table IV.

TABLE IV

Neuropharmacological Profile

| Compound Example No. | Dose (mg/kg) | CNS Activity |
|---|---|---|
| 3 | 300,100,30,10 | Antidepressant |
| 4 | 300,100,30 | " |
| 5 | 300,100,30,10 | " |
| 10 | 300,100,30 | " |
| 11 | 300,100 | Hypnotic |
| 12 | 300,100,30 | " |
| 19 | 300,100,30,10,3 | Sedative |
| 25 | 300,100,30,10 | Antidepressant |
| 48 | 300,100,30 | Muscle Relaxant |
| 65 | 300,100,30 | Antidepressant |
| 73 | 300,100 | Hypnotic |
| 104 | 300,100,30 | " |

As a consequence of the levels of activity in the carrageenin anti-inflammatory assay, certain of the compounds of the invention were subjected to more advanced evaluation utilizing the adjuvant-induced arthritis test. This test requires one month (from day 0 to day 31) for completion. In the first 17 days (0–17), the disease is in the developing stage, while for the remainder of the month (18–31) the disease is fully developed. The results of this assay procedure, given in terms of percent reduction of swelling in the hind paw of the rat are shown in table V.

The method employed is essentially that of Newbould, Brit. J. Pharmacol. 21:127, 1963. The test compounds were studied in the developing arthritis state and in the established arthritic state. Separate groups of 12 rats were orally administered the compounds using methylcellulose as the vehicle. In the study of the developing disease, administration of the test compounds begins on day 1 and on day 2 each animal is injected with 0.5 ml/kg of a 0.5% suspension of heat-killed *Mycobaterium tuberculosis* into the plantar surface of the left hind paw. Foot volumes were measured by a water displacement device on the day of administration of the Mycrobacterium and again on days 3, 10 and 17. The test compounds were administered once daily. At the same time, body weights were recorded daily and the animals examined for the spread of the inflammation and degree of secondary lesions. For study in the established disease, another group of rats were injected with the Mycrobacterium and foot volumes were measured. After 20 days volumes were again measured and administration of the test compounds began and continued for 11 days. Foot volume measurements were repeated on day 27 and day 31. The extent of the spread of inflammation and degree of lesions were recorded daily as were the body weights. The effect of the test compounds is measured by the percentage reduction in left hind paw volumes as compared to the hind paw volumes of the control groups.

TABLE V

| | Adjuvant-Arthritis Assay (% Reduction) | | | | | | |
|---|---|---|---|---|---|---|---|
| Compound Example No. | Dose (mg/kg) | Day 3 | Day 10 | Day 17 | Day 20 | Day 27 | Day 31 |
| 2 | 40 | 39 | 23 | 0 | | | |
|  | 80 | 40 | 18 | 0 | | | |
|  | 120 | 30 | 13 | 21 | | | |
| 7 | 50 | 30 | 30 | 39 | 4 | 24 | 29 |

As indicated previously, certain of the compounds of the invention also display excellent antipyretic activity. As shown by the following comparative data, 3-methoxy-5-phenyl-1,2,4-triazine (compound of example 2), for instance, is comparable in activity to aspirin. Antipyretic activity was measured utilizing the conventional yeast induced fever assay procedure (15% yeast solution injected at two sites).

TABLE VI

| Antipyretic Assay | | | |
|---|---|---|---|
| | temps. at 0 hr. | Test Compounds Administered & temps. at 18 hrs. | temps. at 19½ hrs. |
| Compound of Example 2 at 100 mg/kg | 38.1 | 39.0 | 35.3 |
| Controls (methylcellulose) | 38.2 | 39.4 | 39.6 |
| Aspirin at 100 mg/kg | 38.0 | 38.8 | 37.8 |

As indicated by the test data presented hereinabove, the compounds of the present invention evidence a high degree of pharmacological activity. Moreover, the present compounds possess certain advantageous properties which make them particularly interesting for use in the aforementioned methods and compositions of the invention. For example, the preferred substituted 1,2,4-triazine compounds of the invention, as a consequence of the absence of any acid forming groups thereon, are presently considered non-ulcerogenic. Moreover, the present compounds are nonsteroidal and, accordingly, are devoid of the adverse side effects often associated with steroids. Some of the preferred hypotensive compounds of the present invention, e.g., the compound of example 7, demonstrate both advantageous rapid onset of action as well as a long duration of activity which are particularly valuable properties in the chemotherapeutic management of hypertension. It is also important to note that the preferred 5-substituted compounds of the invention are relatively more soluble in water and organic solvents than previously suggested 5,6-disubstituted compounds which is specifically advantageous from a formulation standpoint.

While the invention has been described and illustrated with reference to certain preferred embodiments thereof, those skilled in the art will appreciate that various changes, modifications, and substitutions can be made therein without department from the spirit of the invention. For example, effective dosages other than the preferred ranges set forth hereinabove may be applicable as a consequence of variations in the responsiveness of the mammal treated, severity of observed conditions, i.e., inflammation, fever, pain, etc., dosage related adverse effects, if any, observed and analogous considerations. Likewise, the specific pharmacological responses observed may vary depending upon the particular active compound selected or whether different active compounds are used in combination or in the presence of suitable pharmaceutical carriers as well as the type of formulation and mode of administration employed and such expected variations or differences in results are contemplated in accordance with the objects and practices of the present invention. It is intended, therefore, that the invention be limited only by the scope of the claims which follow.

What is claimed is:

1. A compound selected from the group consisting of compounds of the formula

wherein
$R_1$ is $C_1-C_4$ hydroxy alkylamino, N-($C_1-C_2$ alkyl)-N-(hydroxy $C_1-C_4$ alkyl)amino, $C_1-C_4$ alkyl, $C_1-C_{10}$ alkoxy, $C_6-C_{10}$ aryloxy, $C_3-C_6$ cycloalkoxy, phenyl alkoxy, allyloxy, halophenoxy, $C_1-C_4$ alkyl phenoxy, $C_1-C_4$ alkoxy phenoxy, $C_1-C_{10}$ alkylthio, $C_3-C_6$ cycloalkylthio, $C_1-C_4$ alkyl sulfinyl, $C_1-C_4$ alkyl sulfonyl, phenyl $C_1-C_4$ alkylthio, dimethylpyrrolidyl, hydrazino, $C_1-C_4$ alkyl hydrazino, or the group

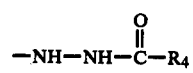

where $R_4$ is $C_1-C_8$ alkyl, $C_1-C_8$ alkenyl, halo ($C_1-C_8$) alkyl, halo ($C_1-C_8$) alkenyl, $C_6-C_{10}$ cycloalkyl or $R_4$ represents the group

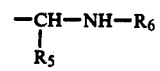

where $R_5$ is H, $C_1-C_4$ alkyl or benzyl and $R_6$ is H or carbobenzyloxy;

$R_2$ represents hydrogen, $C_1-C_4$ alkyl, $C_3-C_6$ cycloalkyl, adamantyl, furyl, thienyl, benzofuryl, indolyl, pyridyl, halothienyl, phenyl or phenyl substituted with at least one substituent selected from halo, $C_1-C_6$ alkyl, halo $C_1-C_6$ alkyl, $C_1-C_6$ alkoxy, acetamido, benzyloxy, diphenylmethyl, morpholino, methylene dioxy or nitro;

and $R_3$ represents hydrogen, $C_1-C_6$ alkyl, pyridyl, furyl, phenyl or phenyl substituted with at least one substituent selected from halo, $C_1-C_6$ alkyl, $C_1-C_6$ alkoxy, methylene dioxy or acetamido;

subject to the provisos that when $R_2$ is hydrogen, $R_3$ is also hydrogen; when $R_1$ is alkyl, phenyl alkylthio, alkoxy, alkylthio, cycloalkylthio, cycloalkoxy, phenyl alkoxy, dimethylpyrrolidyl or hydroxy alkylamino or said N-(alkyl)-N-(hydroxyalkyl)amino as defined before, $R_2$ and $R_3$ cannot both be halophenyl, $C_1-C_3$ alkyl phenyl or $C_1-C_3$ alkoxyphenyl; when $R_1$ is hydrazino, methylthio, methoxy or ethoxy, $R_2$ is other than phenyl and $R_2$ and $R_3$ cannot both be methyl; or when $R_1$ is hydrazino or $C_1-C_4$ alkylhydrazino, $R_2$ is other than $C_1-C_4$ alkyl; and the pharmaceutically acceptable salts thereof.

2. The compound as defined in claim 1 wherein $R_1$ is hydrazino, methyl hydrazino, haloacetyl hydrazino, $C_1$–$C_3$ alkoxy, allyloxy, $C_1$–$C_3$ alkylthio or benzylthio; $R_2$ is $C_3$–$C_6$ cycloalkyl, thienyl, furyl, pyridyl, indolyl, phenyl, meta-halophenyl, methoxy phenyl, dimethoxy phenyl or trifluoromethylphenyl; and $R_3$ is hydrogen, $C_1$–$C_4$ alkyl, pyridyl or furyl.

3. The compound as defined in claim 2 wherein $R_3$ is hydrogen.

4. The compound as defined in claim 2 wherein said compound is selected from the group consisting of 3-acetyl hydrazino-5-phenyl-1,2,4-triazine, 3-propionylhydrazino-5-(4'-chlorophenyl)-1,2,4-triazine, 3-methyl hydrazino-5-phenyl-1,2,4-triazine, 3-acetylhydrazino-5,6-diphenyl-1,2,4-triazine, 3-methylhydrazino-5,6-bis(4'-chlorophenyl)-1,2,4-triazine, 3-trifluoroacetyl hydrazino-5-phenyl-1,2,4-triazine, 3-methoxy-5-t-butyl-1,2,4-triazine, 3-methoxy-5-(3'-trifluoromethyl-phenyl)-1,2,4-triazine, 3-methoxy-5,6-dipyridyl-1,2,4-triazine, 3-methylthio-5-t-butyl-1,2,4-triazine, 3-methylthio-5-(2'-furyl)-1,2,4-triazine, 3-methylthio-5-(2'-thienyl)-1,2,4-triazine, 3-methylthio-5-(3'-trifluoromethylphenyl)-1,2,4-triazine, 3-n-propoxy-5-phenyl-1,2,4-triazine, 3-methylthio-5-(3'-indolyl)-1,2,4-triazine, 3-methylthio-5-cyclopropyl-1,2,4-triazine, 3-methoxy-5-cyclopropyl-1,2,4-triazine, 3-allyloxy-5-phenyl-1,2,4-triazine, 3-allyloxy-5,6-dimethyl-1,2,4-triazine, 3-hydrazino-5-(3'-trifluoromethyl phenyl)-1,2,4-triazine, 3-methoxy-5-(3'-chlorophenyl)-1,2,4-triazine, 3-methoxy-5-(4'-morpholino phenyl)-1,2,4-triazine, 3-α-aminoacetyl hydrazino-5-phenyl-1,2,4-triazine, and 3-α-aminopropionyl hydrazino-5-(4'-chlorophenyl)-1,2,4-triazine.

5. The compound is defined in claim 4 wherein said compound is 3-trifluoroacetyl hydrazino-5-phenyl-1,2,4-triazine.

6. The compound as defined in claim 4 wherein said compound is 3-methoxy-5-(3'-chlorophenyl)-1,2,4-triazine.

7. The compound as defined in claim 4 wherein said compound is 3-methyl hydrazino-5-phenyl-1,2,4-triazine.

8. A hypotensive composition comprised of a compound of the formula

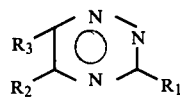

wherein
$R_1$ is hydroxy $C_2$–$C_4$ alkylamino, $C_1$–$C_4$ alkoxy, $C_1$–$C_4$ alkylthio, hydrazino, $C_1$–$C_4$ alkyl hydrazino, or the group

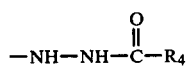

where $R_4$ is $C_1$–$C_8$ alkyl, $C_1$–$C_8$ alkenyl, halo ($C_1$–$C_8$) alkyl, halo ($C_1$–$C_8$) alkenyl, $C_6$–$C_{10}$ cycloalkyl or $R_4$ represents the group

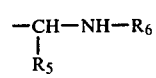

where $R_5$ is H, $C_1$–$C_4$ alkyl or benzyl and $R_6$ is H or carbobenzyloxy;
$R_2$ represents furyl, benzofuryl, phenyl or phenyl substituted with at least one substituent selected from halo, halo $C_1$–$C_2$ alkyl, $C_1$–$C_4$ alkoxy, methylene dioxy or morpholino when $R_3$ represents hydrogen; or wherein $R_1$ represents hydrazino, $C_1$–$C_4$ alkoxy or the group

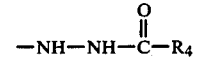

where $R_4$ is $C_1$–$C_8$ alkyl, $C_1$–$C_8$ alkenyl, halo ($C_1$–$C_8$) alkyl, halo ($C_1$–$C_8$) alkenyl, $C_6$–$C_{10}$ cycloalkyl or a group of the formula

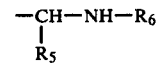

where $R_5$ is H, $C_1$–$C_4$ alkyl or benzyl and $R_6$ is H or carbobenzyloxy and $R_2$ and $R_3$ are the same and selected from phenyl, substituted phenyl or furyl; and the pharmaceutically acceptable salts thereof and a pharmaceutical carrier.

9. The composition as defined in claim 8 wherein said compound is selected from the group consisting of 3-methylhydrazino-5-phenyl-1,2,4-triazine, 3-α-aminoacetyl hydrazino-5-phenyl-1,2,4-triazine, 3-α-aminopropionylhydrazino-5(4'-chloro-phenyl)-1,2,4-triazine, 3-trifluoroacetyl hydrazino-5-phenyl-1,2,4-triazine, 3-propionyl hydrazino-5-phenyl-1,2,4-triazine, 3-hydrazino-5-(3'-trifluoromethylphenyl)-1,2,4-triazine and 3-methoxy-5-(4'-methoxyphenyl)-1,2,4-triazine.

10. A pharmaceutical preparation in dosage unit form adapted for administration to obtain a hypotensive effect, comprising, per dosage unit, a hypotensively effective amount within the range of from about 1 to about 300 milligrams of at least one compound of the formula

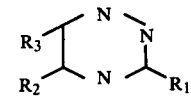

wherein
$R_1$ is hydroxy $C_2$–$C_4$ alkylamino, $C_1$–$C_4$ alkoxy, $C_1$–$C_4$ alkylthio, hydrazino, $C_1$–$C_4$ alkyl hydrazino, or the group

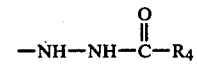

where
$R_4$ is $C_1$–$C_8$ alkyl, $C_1$–$C_8$ alkenyl, halo ($C_1$–$C_8$) alkyl, halo ($C_1$–$C_8$) alkenyl, $C_6$–$C_{10}$ cycloalkyl or $R_4$ represents the group

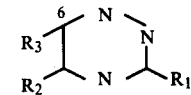

where $R_5$ is H, $C_1$–$C_4$ alkyl or benzyl and $R_6$ is H or carbobenzyloxy;
$R_2$ represents furyl, benzofuryl, phenyl or phenyl substituted with at least one substituent selected from halo, halo $C_1$-$C_2$ alkyl, $C_1$-$C_4$ alkoxy, methylene dioxy or morpholino when $R_3$ represents hydrogen; or wherein $R_1$ represents hydrazino, $C_1$-$C_4$ alkoxy or the group

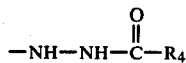

where
$R_4$ is $C_1$-$C_8$ alkyl, $C_1$-$C_8$ alkenyl, halo ($C_1$-$C_8$) alkyl, halo ($C_1$-$C_8$) alkenyl, $C_6$-$C_{10}$ cycloalkyl or a group of the formula

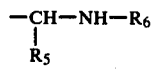

where
$R_5$ is H, $C_1$-$C_4$ alkyl or benzyl and $R_6$ is H or carbobenzyloxy and $R_2$ and $R_3$ are the same and selected from phenyl, substituted phenyl or furyl; and the pharmaceutically acceptable salts thereof and a pharmaceutical carrier.

11. A method of obtaining a hypotensive effect, comprising administering the pharmaceutical preparation as defined in claim 10 to an animal in need thereof.

12. A method of promoting a hypotensive effect in an animal in need thereof, comprising administering thereto a hypotensively sufficient amount of a compound of the formula

wherein
$R_1$ is hydroxy $C_2$-$C_4$ alkylamino, $C_1$-$C_4$ alkoxy, $C_1$-$C_4$ alkylthio, hydrazino, $C_1$-$C_4$ alkyl hydrazino, or the group

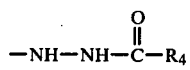

where $R_4$ is $C_1$-$C_8$ alkyl, $C_1$-$C_8$ alkenyl, halo ($C_1$-$C_8$) alkyl, halo ($C_1$-$C_8$) alkenyl, $C_6$-$C_{10}$ cycloalkyl or $R_4$ repreents the group

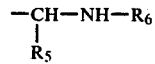

where
$R_5$ is H, $C_1$-$C_4$ alkyl or benzyl and $R_6$ is H or carbobenzyloxy;
$R_2$ represents furyl, benzofuryl, phenyl or phenyl substituted with at least one substituent selected from halo, halo $C_1$-$C_2$ alkyl, $C_1$-$C_4$ alkoxy, methylene dioxy or morpholino when $R_3$ represents hydrogen; or wherein $R_1$ represents hydrazino, $C_1$-$C_4$ alkoxy or the group

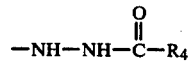

where $R_4$ is $C_1$-$C_8$ alkyl, $C_1$-$C_8$ alkenyl, halo ($C_1$-$C_8$) alkyl, halo ($C_1$-$C_8$) alkenyl, $C_6$-$C_{10}$ cycloalkyl or a group of the formula

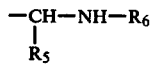

where $R_5$ is H, $C_1$-$C_4$ alkyl or benzyl and $R_6$ is H or carbobenzyloxy and $R_2$ and $R_3$ are the same and selected from phenyl, substituted phenyl or furyl; and the pharmaceutically acceptable salts thereof and a pharmaceutical carrier.

13. The method of claim 12 wherein said compound is 3-trifluoroacetyl hydrazino-5-phenyl-1,2,4-triazine.

UNITED STATES PATENT OFFICE
CERTIFICATE OF CORRECTION

PATENT NO. : 4,157,392

DATED : June 5, 1979

INVENTOR(S) : James M. Gullo et al.

It is certified that error appears in the above-identified patent and that said Letters Patent are hereby corrected as shown below:

Column 1, lines 65-66, "triazine" should be -- triazines -- .
Column 2, line 20, "method" should be -- methods -- .
Column 3, line 10, "helophenoxy" should be -- halophenoxy -- ; line 11, after "alkoxyphenoxy", insert -- $C_1$-$C_{10}$ alkylthio, -- ; line 12, insert a comma after "kylthio".
Column 6, line 15, "metal-trifluoromethyl" should be -- meta-trifluoromethyl -- ; line 56, "doseresponse" should be -- dose-response --.
Column 7, line 26, "represent" should be -- represents -- ; line 42, "pharmacoligical" should be -- pharmacological -- .
Column 12, line 36, "5" should be -- S -- .
Column 14, line 59, "Examples 17-11" should be -- Examples 17-111 -- .
Column 16, line 48, insert a parenthesis after "amino".
Column 20, after Table I, insert -- [1]Comparative Example - See U.S. Pat. No. 3,948,894 -- ; line 38, insert -- a -- after "in"; in Table II, Compound Example Nos. 7, 8, 9 and 10 should each be moved up one line.
Column 28, in Claim 10, beginning line 60, delete formula and insert $$-\underset{\underset{R_5}{|}}{C}H-NH-R_6$$

Column 30, in Claim 12, line 7, "repreents" should be -- represents -- .

Signed and Sealed this

Twenty-seventh Day of November 1979

[SEAL]

Attest:

RUTH C. MASON
Attesting Officer

LUTRELLE F. PARKER
Acting Commissioner of Patents and Trademarks